United States Patent
Allahverdi et al.

(10) Patent No.: US 11,524,926 B2
(45) Date of Patent: Dec. 13, 2022

(54) MAXIMIZATION OF LIGHT OLEFINS IN FCC PROCESS

(71) Applicant: Johnson Matthey Process Technologies, Inc., Savannah, GA (US)

(72) Inventors: Mehdi Allahverdi, Savannah, GA (US); Paul Diddams, Prague (CZ); Charles Kanyi, Savannah, GA (US)

(73) Assignee: Johnson Matthey Process Technologies, Inc., Savannah, GA (US)

( * ) Notice: Subject to any disclaimer, the term of this patent is extended or adjusted under 35 U.S.C. 154(b) by 0 days.

(21) Appl. No.: 17/448,454

(22) Filed: Sep. 22, 2021

(65) Prior Publication Data

US 2022/0106240 A1   Apr. 7, 2022

Related U.S. Application Data

(60) Provisional application No. 63/198,260, filed on Oct. 7, 2020.

(51) Int. Cl.
*C07C 4/06* (2006.01)
*B01J 29/46* (2006.01)

(52) U.S. Cl.
CPC .............. *C07C 4/06* (2013.01); *B01J 29/46* (2013.01); *C07C 2529/46* (2013.01)

(58) Field of Classification Search
CPC ........ C07C 4/06; C07C 2529/46; B01J 29/46; C10G 11/02; C10G 11/05
See application file for complete search history.

(56) References Cited

U.S. PATENT DOCUMENTS

| | | | |
|---|---|---|---|
| 6,852,214 B1* | 2/2005 | Chester | B01J 29/7838 208/120.25 |
| 8,658,024 B2 | 2/2014 | Long | |
| 2016/0216242 A1* | 7/2016 | Ravichandran | G01N 31/10 |
| 2017/0282165 A1 | 10/2017 | Hodoshima | |

OTHER PUBLICATIONS

Yajun, Ji, et al., "Synthesis of isomorphous MFI nanosheet zeolites for supercritical catalytic cracking ofn-dodecane," Applied Catalysis A : General, Elserver, Amsterdam NL, vol. 533, Jan. 16, 2017; pp. 90-98.

* cited by examiner

*Primary Examiner* — Thuan D Dang

(74) *Attorney, Agent, or Firm* — Kevin M. Carroll

(57) ABSTRACT

The invention includes a fluid catalytic cracking process that comprises reacting a hydrocarbon feedstock under catalytic cracking conditions in the presence of a FCC catalyst and an additive, wherein the additive comprises a ZSM-5 molecular sieve having iron in the framework, wherein the process increases production of propylene compared to a process without using the additive. The invention also includes an additive for maximizing production of olefins, which comprises a ZSM-5 molecular sieve having iron in the framework.

10 Claims, 2 Drawing Sheets

FIGURE 1: Propylene make vs Ratio of Framework Fe:Al
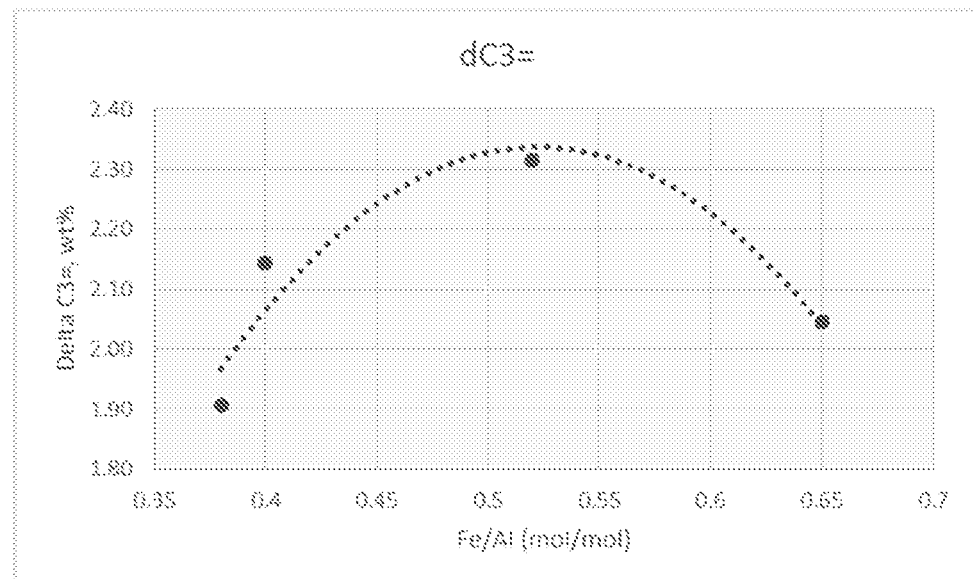

FIG. 2: Propylene make vs P(Fe + Al) molar ratio
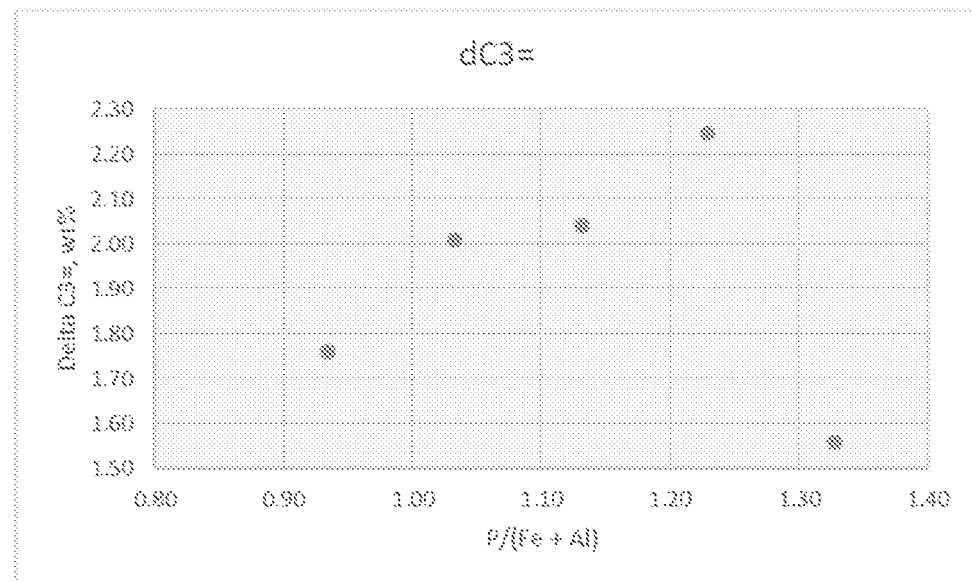

MAXIMIZATION OF LIGHT OLEFINS IN FCC PROCESS

FIELD OF THE INVENTION

The invention relates to a process for maximizing the production of light olefins, in particular propylene, in a fluid catalytic cracking process, and an additive for maximizing production of olefins.

BACKGROUND OF THE INVENTION

The fluid catalytic cracking ("FCC") process produces lighter, valuable products, such as gasoline, distillate, and $C_2$-$C_4$ olefins and saturated hydrocarbons, by the cracking of heavy hydrocarbon fractions. The FCC process can be advantageously used for the production of propylene.

The FCC process typically occurs in the presence of an FCC catalyst. Typical FCC catalyst include Y zeolites, or aluminum deficient forms of these zeolites, such as dealuminized Y, ultrastable Y, and ultrahydrophobic Y. The zeolites may be stabilized with rare earth metals such as lanthanum, cerium, neodymium and praseodymium, for example, in an amount of about 0.1 to about 10 weight %. Catalysts used in FCC processes are in particle form, usually have an average particle size in the range of 20 to 200 microns, and circulate between a cracking reactor and a catalyst regenerator of an FCC unit. In the reactor, hydrocarbon feed contacts hot, regenerated catalyst which vaporizes and cracks the feed at about 400° C. to 700° C., usually 500° C. to about 550° C.

The product distribution from current FCC processes comprises a number of constituents, with gasoline or diesel being of primary interest to most refiners. Light olefins and liquified petroleum gas ("LPG") are also found in the FCC product, and are increasingly becoming of interest to refiners as those products become more valuable. The light olefins produced can be used for a number of purposes, e.g., they are upgraded via sulfuric or HF alkylation to high quality alkylate. LPG is used for cooking and/or heating purposes. Accordingly, operators of FCC units can vary the content of their products depending upon the markets they are serving and the value associated with each of the components found in an FCC product.

Propylene is a particular light olefin in high demand. It is used as a raw material in many of the world's largest and fastest growing synthetic materials and thermoplastics. Refiners are relying more and more on their FCC units to meet the increased demand for propylene, thus shifting the focus of the traditional FCC unit away from transportation fuels and more toward petrochemical feedstock production as operators seek opportunities to maximize margins.

Previously disclosed processes teach a catalytic conversion process of petroleum hydrocarbons, in particular, to a catalytic conversion process for producing light olefins with a high yield from petroleum hydrocarbons processes. See for example, U.S. Pat. Nos. 5,997,728 and 8,658,024 and U.S. Pat. Appl. Publ. Nos. 2005/0020867 and 2010/0010279.

U.S. Pat. Appl Publ. No. 2009/0134065 teaches a fluidizable catalyst composition comprising a pentasil zeolite, at least five percent by weight phosphorus (as $P_2O_5$), and at least about 1% iron oxide present outside the pentasil framework.

Industrial facilities are continuously trying to find new and improved methods to produce light olefins, especially those refiners that are also interested in producing gasoline as primary product from their FCC unit. Thus, it is desirable to have an additive that enhances olefins selectivity, e.g., propylene selectivity, on a unit LPG basis, relative to the selectivity of existing additives.

Applicants have developed a process and additive to increase propylene make by approximately 15% compared to previous processes.

SUMMARY OF THE INVENTION

The invention includes a fluid catalytic cracking process that comprises reacting a hydrocarbon feedstock under catalytic cracking conditions in the presence of a FCC catalyst and an additive, wherein the additive comprises a ZSM-5 molecular sieve having iron in the framework. The process increases production of propylene compared to a process without using the additive. The invention also includes an additive comprising a ZSM-5 molecular sieve having iron in the framework.

BRIEF DESCRIPTION OF THE DRAWINGS

FIG. 1 shows a plot of propylene make vs the molar ratio of framework iron to framework aluminum (Fe:Al).

FIG. 2 shows a plot of propylene make vs the molar ratio of phosphorus to the combined amount of framework iron and framework aluminum (P:(Fe+Al)).

DETAILED DESCRIPTION OF THE INVENTION

The invention includes a fluid catalytic cracking process for the catalytic cracking of hydrocarbon feedstock comprising contacting the feedstock under catalytic cracking conditions in the presence of a FCC catalyst and an additive. Preferably, the catalytic cracking conditions comprise reacting the hydrocarbon feedstock at a temperature from about 400° C. to about 700° C. The contacting of the feedstock typically occurs in a FCC unit that comprises a riser and a reaction section in which the FCC catalyst contacts and vaporizes a hydrocarbon feedstock. The hydrocarbon feedstock preferably enters the bottom of the riser of the FCC unit and carries the FCC catalyst and the additive up the riser into the reactor section. Cracked hydrocarbon product exits the top of the reactor and FCC catalyst particles and additive are retained in a bed of particles in the lower part of the reactor.

The used FCC catalyst and additive are then passed to the regenerator of the FCC unit. As used in this application, the term "regenerator" also includes the combination of a regenerator and a CO boiler, particularly when the regenerator itself is run under partial burn conditions. In the regenerator, coke on the FCC catalyst and additive is burned off in a fluidized bed in the presence of oxygen and a fluidization gas which are typically supplied by entering the bottom of the regenerator. The regenerated FCC catalyst and additive are withdrawn from the regenerator and returned to the riser for reuse in the cracking process.

Preferably, a circulating inventory of FCC catalyst and additive is circulated in the catalytic cracking process, wherein from about 2% to about 20% by weight of this circulating inventory comprises the additive as described above.

Hydrocarbon feedstocks for the catalytic cracking process can range from petroleum distillates or residual stocks, either virgin or partially refined, coal oils and shale oils, gas oils, vacuum gas oils, atmospheric resids, vacuum resids, biomass, coker gas oil, lube oil extracts, hydrocracker bottoms, wild naphtha, slops, and the like. The feedstock may contain recycled hydrocarbons, such as light and heavy cycle oils which have already been subjected to cracking. Preferred feedstocks include gas oils, vacuum gas oils, atmospheric resids, and vacuum resids.

The additive and FCC catalyst may be added to the FCC unit separately or together. Additives are preferably, but not exclusively, added to the regenerator of an FCC unit.

The additive and FCC catalyst can be introduced into the FCC unit by manually loading from hoppers, bags or drums or using automated addition systems, as described, for example, in U.S. Pat. No. 5,389,236. To introduce the additives to an FCC unit, the additives can also be pre-blended with FCC catalysts and introduced into the unit as an admixture. Alternatively, the additives and FCC catalysts can be introduced into the FCC unit via separate injection systems. In another embodiment, the additives can be added in a varying ratio to the FCC catalyst. A varying ratio can be determined, for example, at the time of addition to the FCC unit in order to optimize the rate of addition of the additives.

Conventional and High Severity FCC riser or downer cracking conditions, or older style FCC fluid bed reactors cracking conditions can be used. Cracking reaction conditions include catalyst/oil ratios of about 1:1 to about 30:1 and a catalyst contact time of about 0.1 to about 360 seconds, and riser top/reactor bed temperatures from about 425° C. to about 750° C.

The additives of the invention can be added to any conventional fluid bed reactor-regenerator systems, to ebullating catalyst bed systems, to systems which involve continuously conveying or circulating catalysts/additives between reaction zone and regeneration zone and the like. In one embodiment, the system is a circulating bed system. Typical of the circulating bed systems are the conventional moving bed and fluidized bed reactor-regenerator systems. Both of these circulating bed systems are conventionally used in hydrocarbon conversion (e.g., hydrocarbon cracking) operations. In one embodiment, the system is a fluidized catalyst bed reactor-regenerator system.

Other specialized riser-regenerator systems that can be used herein include deep catalytic cracking (DCC), millisecond catalytic cracking (MSCC), high severity petrochemical FCC resid fluid catalytic cracking (RFCC) systems, Superflex, Advanced Catalytic Olefins, and the like.

The FCC catalyst of the invention means any catalyst which can be used for operating an FCC unit under all types of catalytic cracking conditions. Any commercially available FCC catalyst can be used as the FCC catalyst. The FCC catalyst can be 100% amorphous, but in one embodiment, can include some zeolite in a porous refractory matrix such as silica-alumina, clay, or the like. The zeolite is usually from about 5 to about 70% of the catalyst by weight, with the rest being matrix. Conventional zeolites such as Y zeolites, or aluminum deficient forms of these zeolites, such as dealuminated Y, ultrastable Y and ultrahydrophobic Y, can be used. The zeolites can be stabilized with magnesium or rare earths, for example, in an amount of from about 0.1 to about 10% by weight.

The zeolites that can be used herein include both natural and synthetic zeolites.

Relatively high silica zeolite containing catalysts can be used in the invention. They can withstand the high temperatures usually associated with complete combustion of coke to $CO_2$ within the FCC regenerator. Such catalysts include those typically containing about 10 to about 70% ultrastable Y or rare earth ultrastable Y.

The additive for use in the process of the invention comprises a ZSM-5 molecular sieve having iron in the framework. The ZSM-5 molecular sieve has a five-membered ring in the structure's framework. The framework comprises silica and alumina in tetrahedral coordination. The ZSM-5 molecular sieve also has iron in the framework. The iron is added to the framework as being part of the process of making ZSM-5. By "in the framework" it is meant iron present within the ZSM-5's structural framework in that it replaces the silicon or aluminum of the typical silica-alumina framework of ZSM-5.

The additive preferably comprises at least 0.5 weight percent iron (as measured as iron oxide), more preferably from 1 to 5 weight percent iron (as measured as iron oxide) in the molecular sieve framework, and even more preferably from about 1 to 3 weight percent iron (as measured as iron oxide).

Preferably, the molar ratio of iron to aluminum in the framework of the ZSM-5 is within the range of 0.4 to 0.67.

The ZSM-5 containing iron in the framework can be produced by any known means. For instance, an alumina, silica, iron, acid, and template sources can be mixed in a controlled way to make molecular sieve gel. The gel is then crystallized at high temperatures (under autogeneous pressure) for a period of time. The ZSM-5 containing framework iron is then processed by preferably filtering, washing, ion exchanging and milling.

Following preparation, the ZSM-5 is preferably ion exchanged with a desired cation to replace alkali metal present in the zeolite as prepared. The exchange treatment is such as to reduce the alkali metal content of the final catalyst to less than about 0.5 weight percent, and preferably less than about 0.1 weight percent.

Preferably, the additive also comprises phosphorus. The phosphorus is typically used to stabilize the ZSM-5.

Preferably, the phosphorus is added to the additive containing ZSM-5 having framework iron as by impregnating the ZSM-5 with a phosphorus compound. Alternatively, the phosphorus can be added to an additive that contains other components such as inorganic oxides in addition to the ZSM-5. The additive preferably comprises at least about five percent by weight phosphorus (as $P_2O_5$), more preferably at least 8 weight percent, and even more preferably at least 10 weight percent.

Any phosphorus-containing compound may be employed to add phosphorus to the ZSM-5. Preferably, the phosphorus-containing compound will contain a covalent or ionic constituent capable of reacting with hydrogen ion. Suitable phosphorus-containing compounds include acids such as phosphoric acid, phosphorous acid, and salts thereof. Other suitable phosphorus-containing compounds include phosphines, phosphites, phosphonates and phosphonites such as primary, secondary, and tertiary, phosphines such as butyl phosphine; tertiary phosphine oxides such as tributylphosphine oxide; primary and secondary phosphonic acids such as benzene phosphonic acid; the esters of the phosphonic acids such as diethyl phosphonate, dialkyl alkyl phosphonates, and alkyl dialkylphosphinates; phosphinous acids, such as diethylphosphinous acid; primary, secondary, and tertiary phosphites; and esters thereof such as the monopropyl ester, alkyl dialkylphosphinites, and dialkyl alkylphosphonite esters.

Preferably, the molar ratio of phosphorus to the combined amount of iron and aluminum in the ZSM-5 framework (P:(Fe+Al)) is in the range of 1 to 1.3.

In addition to the ZSM-5 and phosphorus, the additive preferably contains one or more inorganic oxides. The inorganic oxides are preferably one or more of silica, alumina, silica-alumina, titanium oxide, zirconium oxide, aluminum phosphate, and similar. The inorganic oxides are preferably not a molecular sieve. When the inorganic oxide is an aluminum phosphate, the amount of phosphorus (separate from the aluminum phosphate) added to the additive can be reduced.

The additive preferably also comprises one or more clays. Preferably clays include montmorillonite, kaolin, halloysite, bentonite, attapulgite, and the like.

The additive preferably contains ZSM-5 containing framework iron such that the ZSM-5 comprises 25 to 80 weight percent of the additive, more preferable from 40 to 70 weight percent of the additive.

The additive can be prepared by any known method, including adding the ZSM-5 molecular sieve containing framework iron, phosphorus source, inorganic oxide and clay into the spray dryer feed slurry and forming an additive particle.

Other additives may be used in the process of the invention in addition to the FCC catalyst and the additive of the present invention. Preferably, these additional additives can be added to enhance octane; trap metals; promote CO combustion; to reduce $SO_x$ emissions, $NO_x$ emissions and/or CO emissions; to promote catalysis; or to reduce gasoline sulfur.

The present invention results in enhanced light olefins make compared to similar processes using a ZSM-5 having no added iron, or using a ZSM-5 additive that contains non-framework iron (iron added by ion exchange, incipient wetness, spray dryer feed slurry and/or impregnation).

The following examples merely illustrate the invention. Those skilled in the art will recognize many variations that are within the spirit of the invention and scope of the claims.

Comparative Example 1: Preparation of ZSM-5

Water (about 42 kg) is added to a tank, followed by tetrapropylammonium bromide template (TPABr, 280 g). Waterglass (72 kg; 28.9 wt % $SiO_2$, 8.9 wt % $Na_2O$), aluminum sulfate (12.5 kg; 8.2% $Al_2O_3$), and sulfuric acid (4.45 kg) are then added simultaneously to the tank to maintain a pH of about 9.5. Following the addition of the raw materials, the gel is transferred to a reactor and hydrothermally crystallized at a high temperature (~160° C.) until zeolite relative crystallinity reached 95% or higher (based on a standard ZSM-5 crystal). Following crystallization, the zeolite is washed and ion exchanged to remove sodium. The zeolite is referred to as zeolite 1.

Example 2: Preparation of Zeolite of the Invention Containing Iron in the Framework The procedure of Comparative Example 1 is followed, with the exception ferric sulfate (3.65 kg; 18.2 wt. % $Fe_2O_3$) is added to the tank along with the waterglass, aluminum sulfate, and sulfuric acid; and only 2.8 kg of sulfuric acid is utilized. After all the raw materials were added, the gel was then transferred to reactor and hydrothermally crystallized at a high temperature (~160° C.) until zeolite relative crystallinity was greater than 95%. This zeolite is referred to as zeolite 2.

TABLE 1

Properties of zeolite 1 and 2 are shown in Table 1.

|  | Zeolite 1 | Zeolite 2 |
| --- | --- | --- |
| $Al_2O_3$ (wt %) | 5.23 | 5.19 |
| $Fe_2O_3$ (wt %) | 0.04 | 3.31 |
| $SiO_2$ (wt %) | 94.21 | 91.39 |
| SA ($m^2$/g) | 394 | 413 |

Comparative Example 3: Preparation of Comparative Catalyst Containing ZSM-5

Pseudoboehmite alumina (116.3 g; 78 wt % solids) is added to 630 g of water, and the mixture is mixed for 10 minutes. Formic acid (10.9 g; 90% concentration) is then added and mixture agitated for an hour. This peptized alumina mixture is then transferred to a mix tank, followed by silica sol (263.8 g; 41.3 wt % solids), clay (1177.9 g; 51.6 wt % solids), zeolite 1 (2335.8 g; 35.0 wt % solids), and 85% phosphoric acid (350.5 g). This slurry is stirred for half an hour, and then spray dried to form Catalyst 3.

Example 4: Preparation of Catalyst of the Invention

Catalyst B of the invention is prepared in a similar manner as Example 3 by including use of zeolite 2 in place of zeolite 1, with the exception that 1142.8 g of clay (51.6 wt % solids) and 383.8 g of 85% phosphoric acid are used.

Comparative Example 5: Preparation of Comparative Catalyst with Added Iron as Iron Nitrate Catalyst C was prepared similar manner as Example 4 with the exception that Zeolite 1 (2249.8 g) is used in place of Zeolite 2 and 296.2 g of ferric nitrate (9.8 wt % solids) is also added into the spray dryer feed slurry.

Comparative Example 6: Preparation of Comparative Catalyst with Added Iron as Iron Oxide Catalyst D is prepared in similar manner as Comparative Example 5 but with addition of 29.2 g of ferric oxide (99.5 wt % solids) in place of iron nitrate into the spray dryer feed slurry.

TABLE 2

Properties of Catalysts A, B, C and D

|  | Catalyst A | Catalyst B | Catalyst C | Catalyst D |
| --- | --- | --- | --- | --- |
| $Al_2O_3$ (wt %) | 21.61 | 21.89 | 21.79 | 21.71 |
| $Fe_2O_3$ (wt %) | 0.46 | 1.93 | 2.10 | 2.11 |
| $P_2O_5$ (wt %) | 10.43 | 11.56 | 11.77 | 11.77 |
| $SiO_2$ (wt %) | 66.20 | 63.44 | 63.03 | 63.13 |
| ABD (g/cc) | 0.70 | 0.70 | 0.75 | 0.72 |
| APS (microns) | 77 | 91 | 87 | 89 |
| Attrition (wt %) | 0.4 | 0.5 | 0.2 | 0.3 |
| SA ($m^2$/g) | 146 | 147 | 145 | 140 |

Example 7: Testing of Catalysts A-D

Catalysts A-D are calcined at 732° C. for 1 hour then subjected to steam deactivation. Deactivation is done by steaming at 815° C. for 20 hours at 95% steam. Catalyst testing is conducted using an Advanced Cracking Evaluation (ACE) unit. The catalyst is blended at 4 wt. % with a commercial equilibrium catalyst (Ecat), using a feed which is a mix of vacuum gas oil (80%) and atmospheric residue (20%). Conversion is changed by varying feed amount (at fixed injection rate) while keeping catalyst amount constant.

The activity results are shown in Table 3, as interpolated at constant conversion of 70% with delta yields shown after subtracting from Ecat values.

TABLE 3

Testing of Catalysts A-D

| Delta yield | Catalyst A (Comparative) | Catalyst B | Catalyst C (Comparative) | Catalyst D (Comparative) |
|---|---|---|---|---|
| Conversion (wt %) | 70.00 | 70.00 | 70.00 | 70.00 |
| H2 (wt %) | −0.01 | −0.01 | −0.01 | −0.01 |
| C3⁻ (wt %) | 1.34 | 2.04 | 1.73 | 1.73 |
| C3 (wt %) | 0.18 | 0.27 | 0.27 | 0.24 |
| Total C4⁻ (wt %) | 0.80 | 1.19 | 0.77 | 0.99 |
| iC4 (wt %) | 0.61 | 0.67 | 0.72 | 0.77 |
| nC4 (wt %) | 0.03 | 0.03 | 0.02 | 0.05 |
| LPG (wt %) | 2.97 | 4.28 | 3.44 | 3.71 |
| Coke (wt %) | −0.13 | −0.12 | −0.11 | −0.12 |

As shown in Table 3, Catalyst B, isomorphous framework iron made 52.2 wt % more propylene ($C_3^=$) compared to the corresponding Comparative Catalyst A without isomorphous framework iron, and also made 29.1 wt % more $C_3^=$ compared to either impregnated/mixed Comparative Catalysts C and D.

Example 8: Preparation of Zeolites with Differing Amounts of Framework Iron

Zeolites with different ratios of aluminum and iron are prepared in same manner as Example 2 with exception of the quantities of aluminum and/or iron used. Sulfuric acid was adjusted proportionately to the aluminum and iron.

TABLE 4

Properties of the prepared zeolites are shown in Table 4.

| | Zeolite 3 | Zeolite 4 | Zeolite 5 | Zeolite 6 | Zeolite 7 |
|---|---|---|---|---|---|
| Al₂O₃ (wt %) | 5.16 | 5.51 | 5.58 | 3.79 | 3.43 |
| Fe₂O₃ (wt %) | 3.06 | 4.46 | 5.65 | 3.57 | 4.75 |
| SiO₂ (wt %) | 94.03 | 89.80 | 88.40 | 92.51 | 91.75 |
| SA (m²/g) | 414 | 396 | 388 | 419 | 409 |

Example 9: Preparation of Catalysts with Differing Amounts of Framework Iron

Zeolites 3, 4, and 5, are formulated into catalysts E, F, and G, respectively in similar manner to the process of Example 4. Their properties are shown in Table 5.

TABLE 5

Properties of Catalysts E-G

| | Catalyst E | Catalyst F | Catalyst G |
|---|---|---|---|
| Al₂O₃ (wt %) | 21.57 | 21.61 | 21.59 |
| Fe₂O₃ (wt %) | 1.93 | 2.37 | 2.89 |
| P₂O₅ (wt %) | 11.87 | 11.58 | 11.69 |
| SiO₂ (wt %) | 63.31 | 63.20 | 62.47 |
| ABD (g/cc) | 0.69 | 0.69 | 0.69 |
| APS (microns) | 84 | 92 | 92 |
| Attrition (wt %) | 0.4 | 0.8 | 0.6 |
| SA (m²/g) | 128 | 125 | 125 |

Example 10: Testing of Catalysts with Differing Amounts of Framework Iron

Catalysts B, E, F, and G are calcined, steam deactivated and tested in a similar manner to Example 7. The activity results are shown in Table 6.

TABLE 6

Testing of Catalysts B, E-G

| Delta yield | Catalyst B | Catalyst E | Catalyst F | Catalyst G |
|---|---|---|---|---|
| Conversion (wt %) | 70.00 | 70.00 | 70.00 | 70.00 |
| H2 (wt %) | −0.01 | −0.02 | −0.02 | −0.03 |
| C3⁻ (wt %) | 2.04 | 1.91 | 1.81 | 2.32 |
| C3 (wt %) | 0.27 | 0.23 | 0.34 | 0.28 |
| Total C4⁻ (wt %) | 1.19 | 1.22 | 1.17 | 1.04 |
| iC4 (wt %) | 0.67 | 0.90 | 1.14 | 0.84 |
| nC4 (wt %) | 0.03 | 0.03 | 0.06 | 0.05 |
| LPG (wt %) | 4.28 | 4.29 | 5.05 | 4.27 |
| Coke (wt %) | −0.12 | −0.09 | −0.10 | −0.12 |

The testing results from example 10 are plotted in FIG. 1, showing that maximum benefit (highest propylene yield) with framework iron ZSM-5 is dependent on the ratio of framework aluminum and iron in the zeolite.

Example 11: Preparation of Catalysts with Differing Amounts of Phosphorus

Zeolite 2 (as prepared in Example 2) is formulated into catalysts in same manner as Example 4 but with different levels of phosphorous (9.5 wt %-13.5 wt % $P_2O_5$). The difference is taken out of clay. Properties of the prepared catalysts are shown in Table 7.

TABLE 7

Properties of Catalysts H-K

| | Catalyst H | Catalyst I | Catalyst J | Catalyst K |
|---|---|---|---|---|
| $Al_2O_3$ (wt %) | 22.8 | 22.43 | 21.65 | 21.01 |
| $Fe_2O_3$ (wt %) | 1.72 | 1.65 | 1.62 | 1.62 |
| $P_2O_5$ (wt %) | 9.80 | 10.52 | 12.39 | 13.48 |
| $SiO_2$ (wt %) | 64.37 | 64.15 | 63.15 | 62.74 |
| ABD (g/cc) | 0.71 | 0.71 | 0.71 | 0.71 |
| APS (microns) | 92 | 93 | 99 | 106 |
| Attrition (wt %) | 0.1 | 0.4 | 0.1 | 0.2 |
| SA ($m^2/g$) | 166 | 159 | 140 | 132 |

Example 12: Testing of Catalysts with Differing Amounts of Phosphorus

Catalysts B, H, I, J, and K are calcined, deactivated and tested in similar manner to Example 7.

As shown in Table 8, in addition to activity dependence on ratio of framework Fe/Al, there are other optimization processes required for optimal activity.

TABLE 8

Testing Results for Catalysts B and H-K

| Delta yield | Catalyst B | Catalyst H | Catalyst I | Catalyst J | Catalyst K |
|---|---|---|---|---|---|
| Conversion (wt %) | 70.00 | 70.00 | 70.00 | 70.00 | 70 |
| H2 (wt %) | −0.01 | −0.01 | −0.02 | −0.02 | −0.01 |
| C3⁻ (wt %) | 2.04 | 1.76 | 2.01 | 2.25 | 1.56 |
| C3 (wt %) | 0.27 | 0.21 | 0.30 | 0.30 | 0.22 |
| Total C4⁻ (wt %) | 1.19 | 1.04 | 1.22 | 1.18 | 0.81 |
| iC4 (wt %) | 0.67 | 0.63 | 0.89 | 0.80 | 0.64 |
| nC4 (wt %) | 0.03 | 0.09 | 0.05 | 0.02 | 0.04 |
| LPG (wt %) | 4.28 | 3.66 | 4.55 | 4.56 | 3.26 |
| Coke (wt %) | −0.12 | −0.05 | −0.07 | −0.08 | −0.06 |

The results of Example 12 are plotted in FIG. 2, showing that maximum activity is observed at P/(Fe+Al) mole ratio of about 1.23 (where the Fe and Al are framework).

In summary, over 50% additional propylene is observed with ZSM-5 containing isomorphous framework iron, which is substantially higher than the case where iron is introduced in non-isomorphous forms (either cation exchange or impregnation/mixing). The Fe/Al ratio and P/(Fe+Al) ratio play a crucial role in maximizing the performance benefits.

We claim:

1. A fluid catalytic cracking process comprising reacting a hydrocarbon feedstock under catalytic cracking conditions in the presence of a FCC catalyst and an additive, wherein the additive comprises phosphorus and a ZSM-5 molecular sieve having iron in the framework and the additive has a molar ratio of phosphorus to the combined amount of framework iron and framework aluminum (P:(Fe+Al)) in the range of 1 to 1.3, wherein the process increases production of propylene compared to the same process without using the additive.

2. The fluid catalytic cracking process of claim 1 wherein the hydrocarbon feedstock is reacted at a temperature from about 400° C. to about 700° C.

3. The fluid catalytic cracking process of claim 1 wherein the additive comprises at least four percent by weight phosphorus (as $P_2O_5$).

4. The fluid catalytic cracking process of claim 1 wherein the additive comprises at least about 0.5 weight percent iron, as measured as iron oxide $Fe_2O_3$, in the molecular sieve framework.

5. The fluid catalytic cracking process of claim 1 wherein the ZSM-5 molecular sieve has a molar ratio of framework iron to framework aluminum within the range of 0.4 to 0.67.

6. The fluid catalytic cracking process of claim 1 wherein the additive further comprises one or more inorganic oxides.

7. The fluid catalytic cracking process of claim 6 wherein the inorganic oxide is selected from the group consisting of silica, alumina, silica-alumina, titanium oxide, zirconium oxide, aluminum phosphate, and combinations thereof.

8. The fluid catalytic cracking process of claim 1 wherein the additive further comprises a clay.

9. The fluid catalytic cracking process of claim 1 wherein the ZSM-5 molecular sieve comprises 25 to 80 weight percent of the additive.

10. The fluid catalytic cracking process of claim 1 wherein the ZSM-5 molecular sieve comprises 40 to 70 weight percent of the additive.

* * * * *